United States Patent
Stegmann et al.

(10) Patent No.: US 8,845,572 B2
(45) Date of Patent: Sep. 30, 2014

(54) METHOD AND DEVICE FOR THE TREATMENT OF GLAUCOMA

(75) Inventors: Robert Christopher Stegmann, Pretoria (ZA); Matthias Christian Grieshaber, Binningen (CH); Hans R. Grieshaber, Schaffhausen (CH)

(73) Assignee: Grieshaber Ophthalmic Research Foundation, Schaffhausen (CH)

( * ) Notice: Subject to any disclaimer, the term of this patent is extended or adjusted under 35 U.S.C. 154(b) by 883 days.

(21) Appl. No.: 12/618,326

(22) Filed: Nov. 13, 2009

(65) Prior Publication Data
US 2011/0118649 A1 May 19, 2011

(51) Int. Cl.
- *A61M 5/00* (2006.01)
- *A61F 9/007* (2006.01)
- *A61F 9/00* (2006.01)
- *A61B 19/00* (2006.01)

(52) U.S. Cl.
CPC ........... *A61F 9/00781* (2013.01); *A61F 9/0017* (2013.01); *A61B 2019/5437* (2013.01)
USPC .................................... 604/8; 604/294; 606/6

(58) Field of Classification Search
USPC .................................... 604/8, 9, 294; 606/4–6
See application file for complete search history.

(56) References Cited

U.S. PATENT DOCUMENTS

| | | | |
|---|---|---|---|
| 5,360,399 A * | 11/1994 | Stegmann | 604/521 |
| 5,486,165 A | 1/1996 | Stegmann | |
| 5,487,747 A | 1/1996 | Stegmann | |
| 5,693,062 A | 12/1997 | Stegmann | |
| 6,375,642 B1 * | 4/2002 | Grieshaber et al. | 604/294 |
| 6,726,676 B2 | 4/2004 | Stegmann | |
| 6,764,439 B2 | 7/2004 | Stegmann | |
| 2003/0236484 A1 | 12/2003 | Lynch et al. | |
| 2004/0210181 A1 | 10/2004 | Vass et al. | |
| 2006/0155300 A1 | 7/2006 | Stamper et al. | |
| 2008/0228127 A1 * | 9/2008 | Burns et al. | 604/9 |

FOREIGN PATENT DOCUMENTS

| | | |
|---|---|---|
| AT | 409 586 | 9/2002 |
| EP | 1125568 | 8/2001 |
| EP | 0898947 | 11/2005 |
| WO | WO2005/107664 | 11/2005 |
| WO | WO2007/087061 | 8/2007 |
| WO | WO2008/061043 | 5/2008 |

* cited by examiner

*Primary Examiner* — Melanie Hand
(74) *Attorney, Agent, or Firm* — Henry M. Feiereisen LLC; Ursula B. Day

(57) ABSTRACT

The invention relates to a method and a device for treatment of glaucoma, wherein by means of an elongated catheter provided with a distal portion and a proximal portion, a tube-shaped implant is inserted and released in a Schlemm's canal with two opposite openings exposed by an incision and a folded up scleral flap. In a first phase, the distal portion inserted into the Schlemm's canal through the first opening, while a fluid or gaseous medium is injected at the same time, and exited through the second opening, which is, in circumferential direction, oppositely located. The implant detachably disposed at the protruding distal portion and, in a second phase, inserted, in circumferential direction, into the expanded Schlemm's canal up to the first opening. Subsequently, the distal portion, which protrudes from the first opening, is detached from the implant and, together with the catheter, removed.

26 Claims, 3 Drawing Sheets

METHOD AND DEVICE FOR THE TREATMENT OF GLAUCOMA

The invention relates to a method and a device for the treatment of glaucoma, in which a tube-shaped implant is inserted and released in the Schlemm's canal, which is exposed by an incision and a folded up scleral flap with two opposite openings, by means of a catheter, which is provided with a distal and a proximal portion and which is connected to a pressure source for injecting a gaseous or fluid medium.

BACKGROUND OF THE INVENTION

In a healthy eye, the drainage of the circulating aqueous humor takes place from the rear chamber to the front chamber. The aqueous humor drains in the irido-corneal angle (angulus irido-cornealis) via the trabecular tissue into the circular Schlemm's canal and from there into the blood stream via the episcleral vein system. In pathological conditions of the eye, in particular in the case of resistance due to, for example, a closed Schlemm's canal caused by blockage or some such, continuous drainage of the aqueous humor, which is generated by the epithelial layer of the ciliary body and renewed on an ongoing basis, is oftentimes no longer realized or substantially reduced. As a result, the eye's interior pressure (IOP) can be elevated to such a level that the blood circulation of the optical nerves and, thus, their function is diminished which can lead to the eye disease known as glaucoma and can then lead to blindness of the afflicted eye.

PRIOR ART

A device for the treatment of glaucoma is known from the publication U.S. 2003/0236484 A1, wherein the device includes a tube-shaped catheter having a proximal and a distal portion with an injection unit disposed at the proximal portion and a casing disposed at the distal portion and insertable with the distal portion, through a scleral cut, into the lumen of the Schlemm's canal. Through an insertion motion of the distal portion in circumferential direction, a pressurized medium is injected from the injection unit into the distal portion, as a result of which the casing is expanded in a substantially balloon-like manner so as to expand the circular Schlemm's canal.

From the publications EP 0 898 947 A2 and EP 1 125 568 A2, a respective implant is known which has an elongated tube shape and which is made from flexible biocompatible material. The implant is inserted through a scleral incision into the Schlemm's canal of an eye, whereby the lumen at the target location of the circular Schlemm's canal is retained open, in order to effect the natural drainage of the aqueous humor from the Schlemm's canal via the episcleral vein system.

These techniques in the prior art have however the drawback in that they are mostly temporary in their effect. It would therefore be desirable and advantageous to provide an improved method to obviate prior art shortcomings and to provide a more permanent solution to the drainage problem.

SUMMARY OF THE INVENTION

According to one aspect of the present invention, a method is provided as well as a device for carrying out the method, whereby a permanently controlled circulation of the aqueous humor as well as the natural drainage of the aqueous humor from the front chamber via the trabecular tissue into the Schlemm's canal and from there, via the episcleral vein system, into the blood stream is realized.

Accordingly, the method for treatment of glaucoma includes the steps of providing an incision in the sclera and forming a scleral flap thereby exposing the Schlemm's canal and outward bending of a scleral flap thereby providing access to two openings in the Schlemm's canal which are, in circumferential direction, located opposite each other; inserting a catheter through one of the two openings into a lumen of the Schlemm's canal; simultaneously injecting a fluid or gaseous medium into the Schlemm's canal through the one opening, wherein the Schlemm's canal is expanded; exiting the catheter from another one of the openings, which at least partially protrudes from the other one of the openings; detachably disposing an implant at the exiting catheter and inserting the catheter with the implant circumferentially from the other one of the openings through the expanded Schlemm's canal until the implant reaches the one opening; releasing the implant from the catheter and the catheter from the Schlemm's canal.

In another aspect of the invention, the device for carrying out the afore-stated method includes a catheter having proximal and distal portions; a pressure source connected to the catheter; and a tubular implant insertable into Schlemm's canal that has been exposed by an incision to provide access to two openings located opposite each other, the implant is provided with spaced-apart recesses and ring members and configured for detachable disposition at the distal portion for release in the Schlemm's canal; wherein the distal portion has spaced-apart bores in communication with an interior space of the catheter for injecting a fluid or gaseous medium under pressure from the pressure source into the Schlemm's canal and having at least a length which is oriented, in circumferential direction of the Schlemm's canal, from one of the two openings to the other of the two openings and to partially protrude from the Schlemm's canal, wherein the distal portion has, at its front distal end, a head piece at which the implant is disposed and positively connected.

In a further aspect of the invention, the medium for applying pressure to expand the Schlemm's canal and the implant is a gaseous medium or a fluid medium The present invention resolves prior art problems by providing natural drainage of the aqueous humor of an eye suffering from an eye disease known as glaucoma. The natural drainage of the aqueous humor takes place from the front chamber via the trabecular tissue into the expanded Schlemm's canal, which is, in circumferential direction, provided with the released implant. From there, drainage of the aqueous humor into the blood stream, via the episcleral vein system, is restored and permanently maintained. Thereby a reliable natural regulation of the eye's inner pressure (intraocular pressure IOP) is realized.

BRIEF DESCRIPTION OF THE DRAWING

Other features and advantages of the present invention will be more readily apparent upon reading the following description of currently preferred exemplified embodiments of the invention with reference to the accompanying drawing, in which:

FIG. 13 shows a portion of the catheter with the implant detachably disposed at the catheter;

DETAILED DESCRIPTION OF PREFERRED EMBODIMENTS

Figure 1:
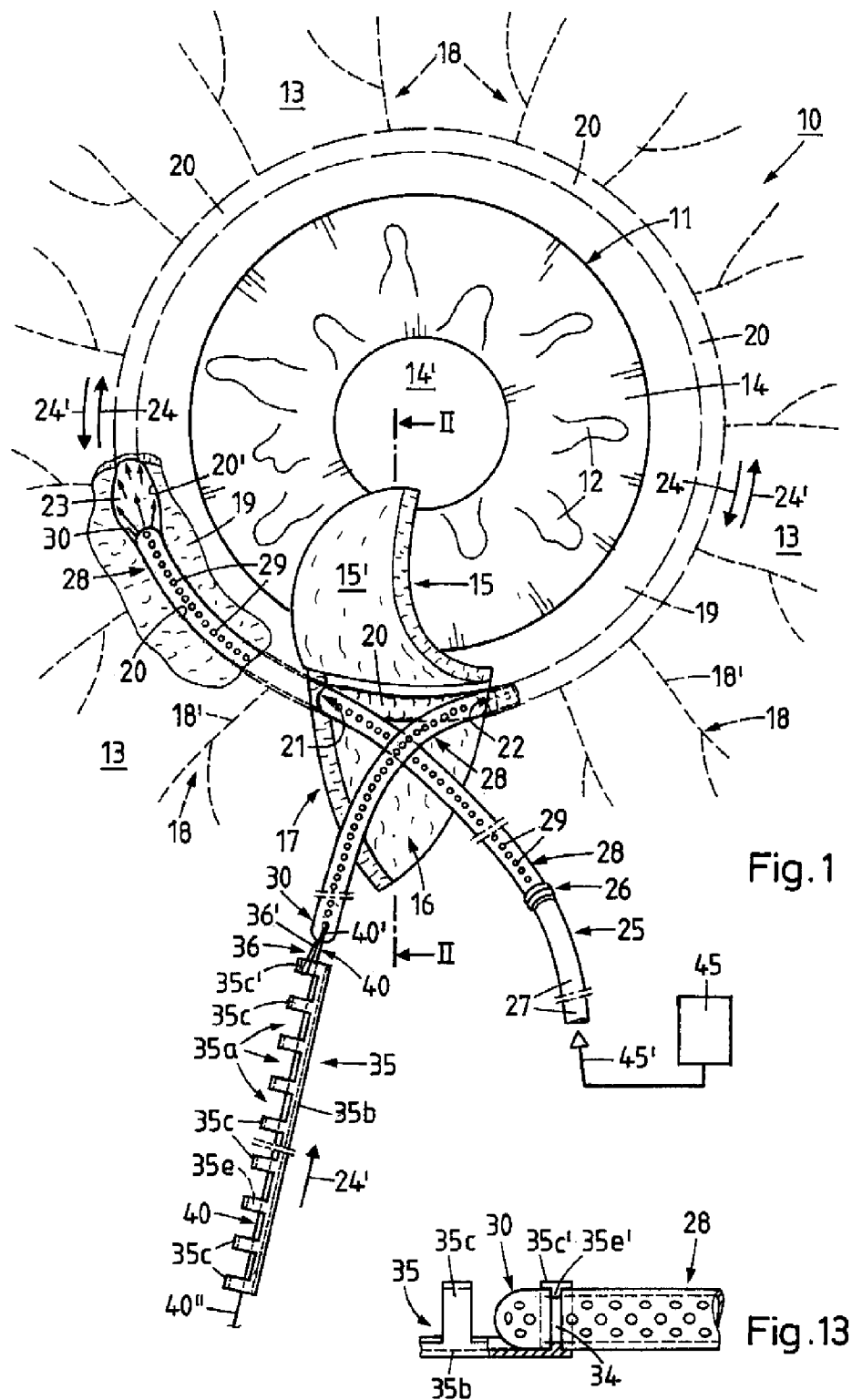
FIG. 1 is a schematic front view of an eye showing Schlemm's canal partially exposed by a lamellar incision for insertion of a catheter and release of an implant.

Throughout all the Figures, same or corresponding elements are generally indicated by same reference numerals.

Figure 2:
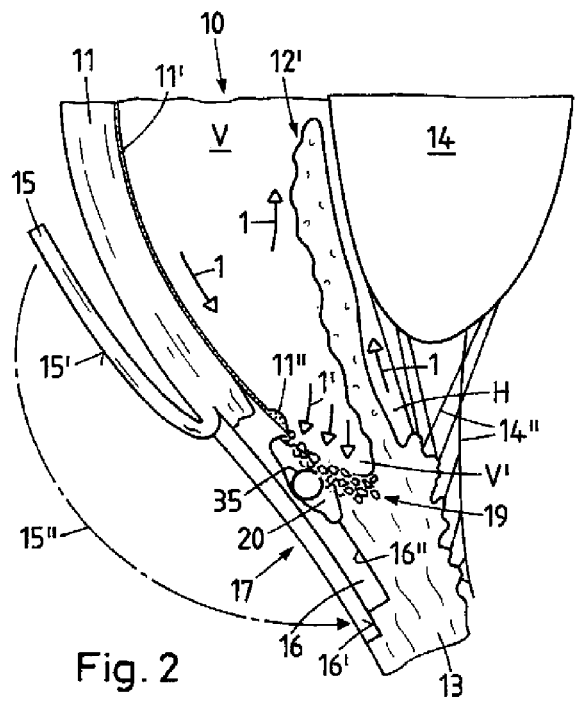
FIG. 2 is a larger scale vertical section view of the eye with the exposed Schlemm's canal and the implant arranged therein, in accordance with line II-II in FIG. 1.

Turning now to the drawing, and in particular for better understanding the problems in connection with glaucoma surgery, FIG. 1 is a schematic front view of an eye 10 and FIG. 2 is a vertical section view of the eye 10. One recognizes the Schlemm's canal, which is partially exposed by the incision into the sclera for insertion of a catheter 25 and an implant 35.

In FIG. 1 there is shown a front view of the eye 10 and the cornea 11 depicted in a schematic view, the iris 12, the sclera 13, the lens 14 with the pupil 14', the trabecular tissue as well as the circular Schlemm's canal 20 (sinus venosus sclerae), which is connected to with the circumferentially distributed aqueous humor channel systems 18 and small canals 18'. Furthermore, FIG. 1 shows the lamellar incision 17 of a size of about 3 mm by 3 mm into the sclera 13 with opened scleral flap 15 as well as the partially opened Schlemm's canal 20. The scleral flap 15, after severing an interior scleral part not shown in detail, is held in open position by means not shown in detail for further surgical procedures. The incision 17 forms a scleral bed 16 (reservoir) which is connected to both oppositely located openings 21 and 22 of the Schlemm's canal 20. After insertion and exposure of the implant 35, the scleral bed 16 is being filled with a highly viscous medium. When the scleral flap 15 is folded down and sewn to the sclera 13 in a manner not shown in detail, the filled-in medium prevents an undesired contact of the inner side 15' of the scleral flap 15 with the inner side 16" (FIG. 2) of the scleral bed 16.

As further shown in FIG. 1, in a first phase, the catheter 25 is inserted with a distal portion 28 into the lumen 23 of the Schlemm's canal 20, for example through the first opening 21 in accordance with the arrow direction 24. The catheter 25, which is made of an elongated flexible tube, includes the distal portion 28, which is provided with a head piece 30, as well as, for example, a proximal portion 27 with the same axial direction, which is disposed at the distal portion 28 via a coupling 26. The proximal portion 27 is connected to a pressure source 45 by means not shown here in detail. Upon insertion of the distal portion 28 into the Schlemm's canal 20, a biocompatible medium, for example a hydrophilic fluid or a gaseous medium, is simultaneously injected into the Schlemm's canal 20 in the direction of arrow 45'. A targeted injection of the medium has the effect that, in the radial direction, the inner wall 20' of the Schlemm's canal 20 is slightly stretched by the medium and that, in the area of the head piece 30, the inner wall is substantially stretched in balloon-like manner by means of bores 31 and 29 that are distributed at the head piece 30 as well as at the outer circumference of the distal portion 28. As a result, the distal portion 28 can be inserted into the circular Schlemm's canal without problem in the arrow direction 24, and the distal portion 28 can be lead through the second opening 22 in order to realize a detachable connection with the implant 35.

At this juncture, it is noted that the distal portion 28, which is insertable into the Schlemm's canal 20 has a length hat extends, in the circumferential direction, at least from the first opening 21 to the oppositely located second opening 22 of the Schlemm's canal. Preferably, however, the distal portion 28 has a length that partially protrudes out of the second opening 22. In a preferred embodiment, the distal portion 28 has a length that is 1.5 to 2 times the circumference of the circular Schlemm's canal 20. The implant 35 can be disposed at the head piece 30 of the distal portion 28, which is lead through the second opening 22 and freely accessible, without additional aids and can be detachably connected therewith.

In a second phase, the implant 35, which is disposed at the head piece 30 with a ring member 35', together with the distal portion 28, is inserted into the lumen 23 of the Schlemm's canal 20 through the second opening 22. Preferably, a suitable hydrophilic fluid is injected at the same time. As a result, the distal portion 28, together with the implant 35 disposed at the distal portion 28, can be successively inserted into the Schlemm's canal 20 in the arrow direction 24'. As soon as the ring member 35c of the implant 35, which is detachably disposed at the head piece 30, reaches the first opening 21, the distal portion 28, together with the catheter 25 of the implant 35, which is arranged and exposed in the Schlemm's canal 20, can be detached and removed in a manner that is not shown here in detail.

In the first embodiment shown in FIG. 1, the implant 35 is detachably disposed at the head piece 30 of the distal portion 28 by means of a surgical thread, for example a thread 36' that is tied as a sling or loop 36. The implant 35 with the distal portion 28 is successively inserted into the Schlemm's canal 20 through the second opening 22 in the arrow direction 24', wherein, at the same time, the Schlemm's canal 20 is expanded by the injected hydrophilic fluid. As soon as the implant 35 reaches the opposite first opening 21, the thread 36' is severed by suitable means and the distal portion 28, together with the catheter 25, is removed.

In a second embodiment, the implant 35 is tightly slid onto the head piece 30 of the distal portion 28 in a manner that is not shown here in detail, for example such that the front ring member 35'c is tight-fitting and jammed to prevent axial movement. Subsequently, the distal portion 28 with the implant 35 disposed at the distal portion 28 is, in the arrow direction 24', successively inserted into the Schlemm's canal 20 through the second opening 22, wherein the Schlemm's canal 20 is thereby expanded by the injected hydrophilic fluid. As soon as the implant 25 reaches the first opening 21, which is opposite of the second opening 22 in the circumferential direction, the pressure of the medium is increased. As a result, the front ring member 35c' of the implant 35, which is provided with a slit-shaped crack, is pressurized and slightly expanded so that the distal portion 28 can be pulled out of the inner space 35e of the ring member 35c' and, together with the catheter 25, removed.

In a further embodiment, the implant 35 is detachably disposed at the distal portion 28 by means of a positively latching rapid connection. In this variant, the head piece 30 of the distal portion 28 is provided with a ring groove 34 and the front ring member 35c' of the implant 35 is provided with at least two latching cams 35e' that are arranged opposite of each other at the circumference of the inner space 35e. Preferably, the latching cams 35e' are configured as circular rings. The configuration of the individual elements for the positive rapid connection of the distal portion 28 and the implant 35 are described in connection with FIGS. 6, 8 and 10.

As is further schematically shown in FIG. 1, a surgical thread 40 that is oriented in the axial direction of the implant 35 can be inserted into the inner space 35e of the implant 35. One end 40' of the thread 40 is disposed at the head piece 30 of the distal portion 28 in a manner that is not shown here in detail and held in an, e.g., jammed manner. The other end 40" of the thread 40 protrudes from the tube-shaped implant 35. The function of the thread 40, which is, together with the implant 35, inserted into the Schlemm's canal 20, is described below in connection with FIG. 3.

In the embodiment shown in FIG. 1, the distal portion 28 is inserted into the Schlemm's canal 20 through the first opening 21. However, it is also possible to first insert the distal portion 28 with the head piece 30 into the Schlemm's canal through the second opening 22 and to lead the distal portion 28 with the head piece 30 through the opposite first opening 21. As shown in FIG. 1, to insert the implant 35 into the Schlemm's canal 20, the implant 35 is detachably disposed at the distal portion 28 of the catheter 25, preferably in such a manner that the recesses 35a as well as the ring members 35c of the implant 35 are arranged at the side facing the trabecular tissue 19.

FIG. 2 is a vertical section view of a portion of the eye 2 along line II-II in FIG. 1. One recognizes a portion of the cornea 11 with the front chamber V of the Decement membrane 11' and Schwalb's line 11" as well as a portion of the sclera 13 and the iris 12' with the lens 14, which is connected to the sclera 13 via zonules 14". Further, FIG. 2 sows the swung open scleral flap 15, which is held in this position for further surgery by means that are not shown here in detail. The depth of the incision 17 is preferably chosen such that that the two opposite openings 21 and 22 (FIGS. 1, 3) of the Schlemm's canal 20 are freely accessible in order to insert the distal portion 28 and the implant 35. The incision 17 forms the scleral bed 16 (reservoir) in the sclera 13. After insertion and release of the implant 35, the sclera bed 16 is filled with a highly viscous medium in a manner that is not shown here in detail. Subsequently, the scleral flap 15 is, in the arrow direction 15", flapped onto the support area 16' of the sclera 13 and sewn therewith in a manner not shown here in detail. The highly viscous medium prevents connecting contact of the inner side 15' of the scleral flap 15 with the inner side 16" of the scleral bed 16. Furthermore, FIG. 2 shows the circulation, which is oriented from the rear chamber H in direction of the front chamber V and which is designated with the arrows 1, and, by the arrows 1', the natural drainage of the aqueous humor from the chamber angle V' into the Schlemm's canal 20 via the trabecular tissue 19.

Figure 3:
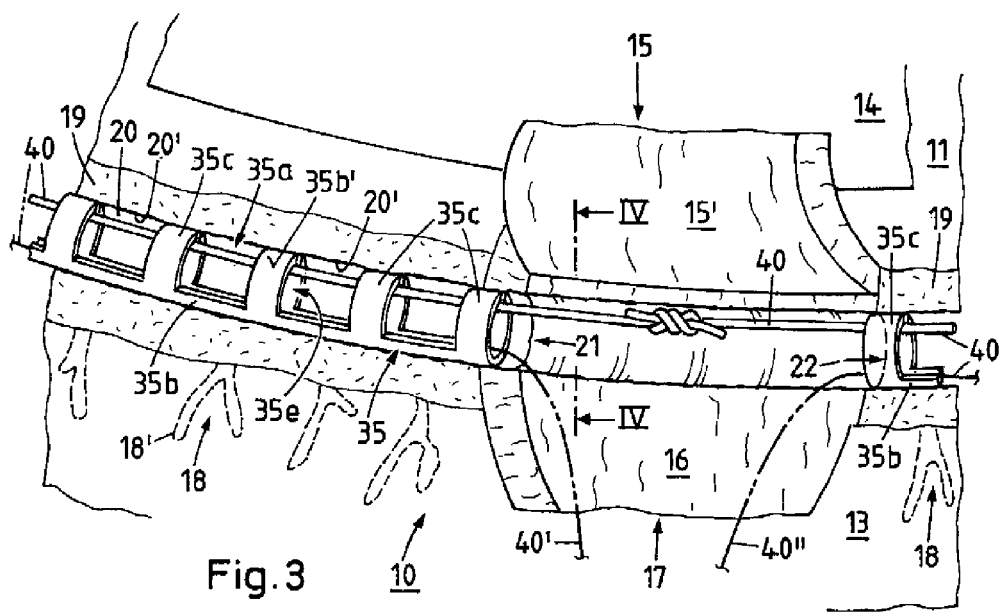
FIG. 3 shows a portion of the eye in larger scale and a partial section view of the eye in accordance with FIG. 1, with the implant inserted and released in the Schlemm's canal and a surgical thread arranged therein.

FIG. 3 shows a portion of the eye 10 in larger scale and depicted in a partial section view with the lamellar incision 17 and the folded-up scleral flap 15 as well as the implant 35, which is inserted into the Schlemm's canal through, for example, the second opening 22 and which is oriented, in circumferential direction, up to the first opening 21. The implant 35, which is partially shown in FIG. 3 and which is provided with the recesses 35a and the ring members 35c, has a length that extends from the second opening 22 in the circumferential direction of the Schlemm's canal 20 to the opposite first opening 21. FIG. 3 further shows the surgical thread 40, which is exposed in the inner space 35e of the implant 35 and schematically depicted by the dashed-and-dotted line, with the two thread ends 40' and 40" protruding from the implant 35. To accomplish an expansion of the trabecular tissue 19, the surgical thread 40 is loaded by means not shown here in detail after release of the implant 35 and after detaching and removing the distal portion 28 and the catheter 25. As a result, the individual ring members 35c of the implant 35 facing the trabecular tissue 19 are loaded in the direction of the front chamber V. Subsequently, the two thread ends 40' and 40" are knotted with each other, as schematically shown in FIG. 3. The thread 40, which is loaded against the inner side of the implant 35, substantially effects an expansion of the trabecular tissue 19 and, as a consequence, increased permeability and improved drainage of the aqueous humor.

Figure 4:
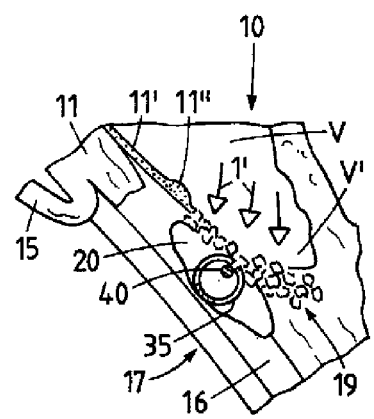
FIG. 4 is a section view of the eye in accordance with line IV-IV shown in FIG. 3, with the implant released in the Schlemm's canal and the surgical thread arranged therein.

FIG. 4 shows a portion of the eye 10 in larger scale and shows a section view of the portion of the eye 10 in accordance with line IV-IV depicted in FIG. 3. One recognizes the front chamber 4 with the chamber angle V', a portion of the cornea 11 with the Decement membrane 11' and the Schwalb's line 11", the lamellar incision 17 with the scleral bed 16 and the folded up scleral flap 15 as well as the Schlemm's canal 20 with the upstream trabecular tissue 19. Further, FIG. 4 shows the implant 35 inserted into the Schlemm's canal 20, which effects the above-mentioned additional circular expansion of the trabecular tissue 19 via the thread 40, which is arranged therein and which is loaded against the inner side of the implant 35.

The catheter 25, which is provided with the proximal and distal portion 27 and 28, as well as the implant 35 and suitable further embodiments thereof are described below in connection with FIGS. 5 to 13.

Figure 5:
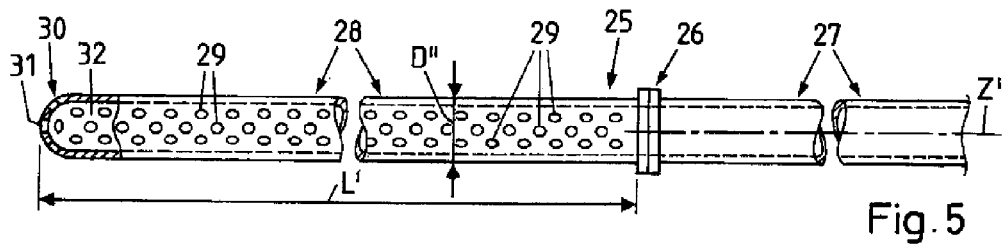
FIG. 5 shows an elevation and partial section view of the catheter, which is provided with a proximal portion and a distal portion.

FIG. 5 shows the catheter 25, which his configured for insertion of the implant 35 and which is made of an elongated flexible small tube or a flexible mini-cannula. The catheter 25 includes the proximal portion 27 with the coupling 26, which is connected to the pressure source 45 (FIG. 1), as well as the distal portion 28 with the head piece 30, which is disposed at the proximal portion 27 in the same axial direction. In a variant that is not shown here, it is possible that the proximal portion 27, which is connected to the pressure source 45, is disposed anywhere on a side of the distal portion 28.

In the embodiment shown in FIG. 5, the two tube-shaped portions 27 and 28 of the catheter 25 have the same axial direction Z' and are detachably connected to each other by means of the schematically shown coupling 26. The distal portion 28 has an outer diameter D", which approximately matches the clear inner diameter D' of the tube-shaped implant 35. Starting from the coupling 26 up to the head piece 30, the distal portion 28 is provided with bores 29, which are distributed in circumferential direction as well as in axial direction and which are connected to the inner space 32 of the distal portion 28. The bores 29, which are essentially configured as pores and operate as respective nozzles, have a diameter of, for example, 10 μm to 25 μm and are bored into the tube-shaped distal portion 28 with laser technology that is known per se and not shown here, preferably with an excimer laser. The head piece 30, which is disposed at the front end of the distal portion 28 and shown in partial section view in FIG.

5, is configured as an approximately semicircular cap and has at least one but preferably multiple distributed bores 31, which are connected to the inner space 32 of the distal portion 28 and which operate as respective nozzles. The distal portion 28 has at the end that is provided with the head piece 30 a length L' of approximately 1.5 to 2 times the circumference of the Schlemm's canal 20.

The head piece 30, which is disposed at the distal portion 28 of the catheter 25 is preferably made of light-reflective, biocompatible material or coated with a light-reflective, biocompatible foil (not shown) or some such. In a further variant, it is possible that the distal portion 28 is, at the distal end, coated with a light-reflective and biocompatible foil or provided with a front portion made of light-reflective and biocompatible material. This ensures that, when the distal portion 28 is inserted into the Schlemm's canal 20, at least the respective position of the front portion or the position of the head piece 30 disposed at the distal portion 28 is reflective due to illumination with a light source that is not shown, so that they are visually well recognizable by the ophthalmologist.

Figure 6:
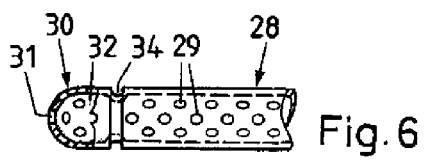
FIG. 6 shows a first variant of a head piece disposed at the distal portion.

FIG. 6 shows a variant of the head piece 30, which is disposed at the distal portion 28 and which is partially depicted in section view. In order to accomplish a detachable rapid connection with the implant 35, the head piece 30 has a ring groove 34, into which a latching cam 35e' disposed at the implant 35 latches in a snapping manner, as shown in FIG. 13.

Figure 7:
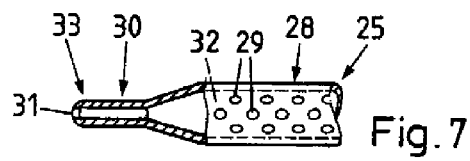
FIG. 7 shows a second variant of the head piece disposed at the distal portion.

FIG. 7 shows a further variant of the head piece 30, which is disposed at the front end of the distal portion 28 and which is partially shown in section view. Starting from the outer diameter D" of the distal portion 28, which is provided with the bores 29, in the direction of a front tip 33, the head piece 30 is, for example, conically tapered and connected with the inner space 32 of the catheter 25 via the bore 31, which operates as a nozzle. A ring groove 34 (cf. FIG. 6), which is not shown in detail here, can be disposed at the head piece 30 shown in FIG. 7 too in order to effect a snapping rapid connection with the implant 35.

Figure 8:
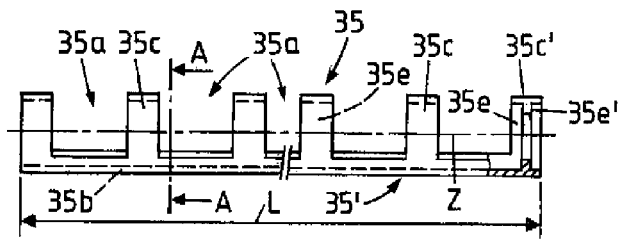
FIG. 8 shows a first embodiment of the implant, in a larger scale elevation view.

FIG. 8 shows, as a first embodiment, the implant 35 made of an elongated flexible small tube 35'. The implant 35 has a connection member 35b, which is oriented in the direction of a longitudinal axis Z and which is, in section view, substantially arc-shaped, and multiple ring members 35, which are disposed at the connection member 35b and which are spaced apart by recesses 35a. The respective ring members 35c provided with the inner space 35e are configured to receive the head piece 30 disposed at the distal portion 28. The ring member 35c', which is disposed at the front distal end of the implant 35 and partial shown in section view, is provided with the latching cam 35e' in the inner space 35e, wherein the latching cam 35e' is oriented in circumferential direction. The stretched length L of the elastically flexible implant 35 corresponds to the circumference of the circular Schlemm's canal 20, which extends from the first opening 21 to the opposite second opening 22. The diameter of an eye is approximately in the order of 10 to 12 mm and is preferably determined before surgery, depending on which the exact stretched length of the implant 35 is calculated.

Figure 9:
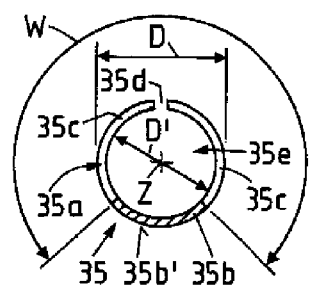
FIG. 9 shows a section view of the implant along section line A-A of FIG. 8.

FIG. 9 shows the implant 35, which is provided with an outer diameter D and a clear inner diameter D' and which is, in section view, configured in an arc shape, in accordance with the section line A-A of FIG. 8. FIG. 9 also shows the connection member 35b, which is oriented in axial direction and configured in an arc shape, as well as the ring member 35c provided with the inner space 35e. The individual ring members 35c are, on the side opposite of the connecting part 35b, separated by a respective slit-shaped crack 35d so that the separated sides of the ring members 35c facing each other are slightly expandable in relation to each other. In a variant that is not shown in detail here, it is possible that the ring members 35c, which are spaced apart as well as sequentially arranged, are alternatively provided as an integral ring member 35c (without crack) or with the slit-shaped crack 35d. Each of the recesses 35a, which are, in axial direction of the implant 35, arranged between the individual ring members 35c, has an opening angle W in the order of 280° to 290°.

Figure 10:
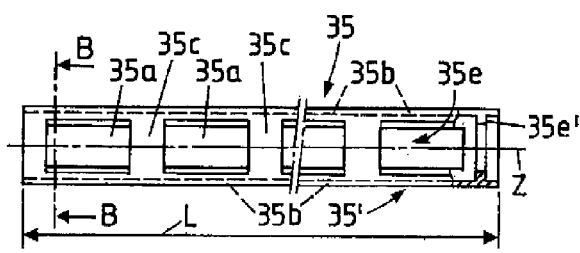
FIG. 10 shows a second embodiment of the implant, in a larger scale elevation view.

FIG. 10 shows a second embodiment of an implant made of an elongated flexible small tube 35', which, in the direction of the longitudinal axis Z, has two connection members 35b, which are arranged diametrically opposite to each other, as well as multiple ring members 35c, which are spaced apart in the direction of the longitudinal axis Z by the recesses 35a. In the shown embodiment, the recesses 35a, which are connected with a respective inner space 35e, are rectangular. However, the recesses 35a can also be oval, elliptic, square or trapezoid, all of which is not shown. The length of the implant 35 according to FIG. 10 is calculated in analogous manner to the above-described implant 35 in connection with FIG. 8.

Figure 11:
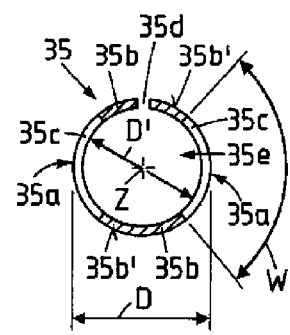
FIG. 11 shows a section view along the section line B-B of FIG. 10.

FIG. 11 shows the implant 35 with the outer diameter D and the inner diameter D', which is, in section view, arc-shaped, in accordance with the section line B-B shown in FIG. 10. FIG. 11 also shows the two connection members 35b, which are arranged diametrically opposite to each other and which are oriented in the direction of the longitudinal axis Z. The connection members 35b are separated by the crack 35d, which is oriented in the direction of the longitudinal axis Z and which is approximately slit-shaped. Furthermore, one recognizes the recesses 35a, each of which is, in circumferential direction, arranged between the connection members 35b and each of which has a limited opening angle W between 90° and 120°. Each of the two connection members 35b, which are arranged diametrically opposite to each other, has an outer arc-shaped support area 35b' that is oriented in the direction of the longitudinal axis Z.

Figure 12:
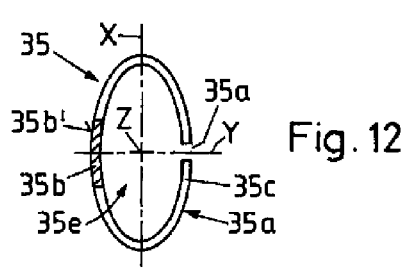
FIG. 12 shows an embodiment of the implant whose cross-section is in the shape of an oval ring.

FIG. 12 shows a further embodiment of the implant 35, which is, in section view, in the shape of an oval ring, for example in the shape of a double-symmetrical oval, which has the longitudinal axis Z as well as the two symmetry axes X and Y. In the case of this implant 35, the connection member 35b, which is provided with the outer support area 35b' and which is oriented in the direction of the longitudinal axis Z, is arranged at the larger arc-shaped side of the oval. At the side opposite of the connection member 35b, the oval ring shaped implant 35 is provided with the slit-shaped crack 35d, which is oriented in the axial direction. In this embodiment, the recesses 35a of the implant 35 have an opening angle W between 280° and 290°.

At this juncture, it is noted that the crack 35d, which is disposed at the implant 35 and oriented in the axial direction of the implant 35, is slit-shaped in such a manner that the sides of the individual ring members 35c facing each other tightly contact each other. As a result, when loading the surgical thread 40 shown in FIGS. 3 and 4, the thread 40 is held in the inner space 35e of the implant 35.

FIG. 13 shows a portion of the distal portion 28, which is provided with the ring groove 34, as well as the implant 35, which is provided with the circular latch cam 35e. The distal portion 28 is, with its head piece 30, inserted into the front distal ring member 35c' of the implant 35 and essentially positively connected with the implant 35 in a snapping manner. Due to the slight spreading of the two parts of the front portion 35c' that face each other, which is caused by the pressure source 45, the distal portion 28 can be detached from the released implant 35 without additional aids and, together with the catheter 25, removed in a manner not shown here in detail.

The tube-shaped implant 35 shown in FIGS. 8 through 12 has an outer diameter D in the order of about 0.2 mm to 0.35 mm and a clear diameter D' in the order of 0.15 mm to 0.25 mm. The maximum length L of the implant 35, which extends, in circumferential direction, from the one opening 21 to the opposite other opening 22 of the Schlemm's canal 20 (FIG. 1) is, as mentioned above, dependent on the diameter of the circular Schlemm's canal 20, which is about 10 to 12 mm.

The implant 35 described above in detail includes an elongated small tube 35c' and is made of, for example, biocompatible material such as plastic, non-corroding steel or stainless steel such as silver, gold, platinum, nitinol or some such, preferably biocompatible flexible material, for example polymeric material having a thermal or mechanical shape memory effect. Due to the implant 35 being made of flexible material having the shape memory effect, the substantially arc-shaped implant 35, which is approximately analogous to the circular Schlemm's canal 20, can be, prior to insertion at a room temperature of about 18° C. to 22° C., disposed at the distal portion 28 of the catheter 25 and inserted into the Schlemms's canal 20 in an approximately straight line and, after release at a body temperature of about 35° C. to 37° C., restored to the shape fitting the arc-shaped inner wall 20' of the circular Schlemm's canal 20. In a variant, it is possible that the implant 35, which is made of the elongated flexible small tube 35', is provided with a biologically active coating, for example a heparin coating.

As shown in FIG. 1, in a first phase, the distal portion 28 of the catheter 25 is inserted into the Schlemm's canal 20, for example through the first opening 21, and, at the same time, the pressure source 45 injects the hydrophilic fluid, for example with low primary pressure, in accordance with the arrow direction 45'. The hydrophilic fluid, which exits the bore 31 of the head piece 30 and the bores 29 of the distal portion 28, simultaneously effects an opening or expansion of the Schlemm's canal 20. In the area of the head piece 30, the Schlemm's canal is expanded in substantially balloon-like manner, as schematically shown in FIG. 1. During the motion, which is oriented in the circumferential direction of the Schlemm's canal 20, the distal portion 28 exits the second opening 22 so much that, subsequently, the implant 35 can be detachably disposed at the head piece 30 of the distal portion 28.

In a second phase, the distal portion 28 is, together with the implant 35 disposed at the distal portion 28, inserted into the Schlemm's canal 20 through the second opening 22 in accordance with the arrow direction 24'. Preferably simultaneously, the pressure source 45 injects the hydrophilic fluid that exits the bores 29 of the distal portion 28 as well as the bores 31 of the head piece 30. As soon as, during the motion oriented in the arrow direction 24', the head piece 30 penetrates the opposite first opening 21 and exits the Schlemm's canal with an appropriate length, the distal portion 28 can be detached from the implant 35 and, together with the catheter 25, removed.

In a preferred embodiment, in a second phase, the surgical thread 40, which penetrates the inner space 35e of the implant 35 in axial direction, can be inserted, together with the implant 35, wherein the surgical thread is disposed with its one end 40' at the distal portion 28 and wherein the other end 40" exits the implant 35. After removal of the distal portion 28 and the catheter 25, the surgical thread is loaded by means not shown here and the two thread ends 40' and 40" are knotted with each other in the area of the incision 17, as schematically shown in FIG. 3. During loading of the thread 40, the trabecular tissue 19 is stretched by the individual ring members 35c of the implant 35 in direction of the front chamber angle V' (FIG. 4), as a result of which the increased permeability and, thus, the improved natural drainage of the aqueous humor is achieved.

During the individual method steps, the head piece 30, which is disposed at the distal portion 28 and made of reflective material or provided with a reflective foil or some such, can be visually well recognized through a surgical microscope during the motion that is oriented in the circumferential direction of the Schlemm's canal 20 in accordance with the arrow direction 24 or 24', so that the respective position of the head piece 30 and the distal portion 28 is exactly verifiable. The head piece 30 is, for example, coated with a reflective fluorescence coat, in which case the reflection ends with one millionth of a second light illumination. The light illumination is preferably effected by means of a light source disposed at the surgical microscope.

The functional elements described above in connection with the individual figures are not limited to the embodiments discussed. Additional embodiments of the catheter 25, particularly of the distal portion 28 with the head piece 30 as well as additional embodiments of the implant 35 are also possible. Furthermore, other biocompatible materials for the individual elements, the coating or the light-reflecting foil are possible with deviating from the fundamental spirit of the invention.

While the invention has been illustrated and described as embodied in a method and device for effecting the drainage of an eye, it is not intended to be limited to the details shown since various modifications and structural changes may be made without departing in any way from the spirit of the present invention. Further practical embodiments of catheter 25, especially the portion 28 with the distal tip 30 and different configurations of the implant 35 for slipping onto the distal portion 28 are possible as well as further biocompatible materials for the respective elements, as well as for the coating and the light-reflecting foil are also possible. The embodiments were chosen and described in order to best explain the principles of the invention and practical application to thereby enable a person skilled in the art to best utilize the invention and various embodiments with various modifications as are suited to the particular use contemplated.

What is claimed is:

1. A system for treating glaucoma, comprising:
   a catheter having proximal and distal portions;
   a pressure source connected to the catheter; and
   a tubular implant insertable into Schlemm's canal that has been exposed by an incision to provide access to two openings located opposite each other, said implant provided with spaced-apart gaps corresponding with an interior space of the implant and bordered by ring members and configured for detachable disposition at the distal portion for release in the Schlemm's canal;
   wherein the distal portion has spaced-apart bores in communication with an interior space of the catheter for injecting a fluid or gaseous medium under pressure from the pressure source into the Schlemm's canal and having at least a length which is oriented, in circumferential direction of the Schlemm's canal, from one of the two openings to the other of the two openings and to partially protrude from the Schlemm's canal;
   wherein the distal portion has, at its front distal end, a head piece at which the implant is disposed and positively connected.

2. The system according to claim 1, further comprising a surgical thread that is tied as a sling or loop, by which the tubular implant is detachably disposed at at least one of the distal portion and the head piece of the distal portion.

3. The system according to claim 1, further comprising a detachable rapid connection, in which the head piece, which is disposed at the distal portion, has a ring groove, and in which the tubular implant, which is coaxially slideable, has at least two latch cams, like implant, which is coaxially slideable, has at least two latch cams, which are arranged opposite of each other at the circumference of an inner space of the tube-like plant and configured to positively and detachably engage during sliding into the ring groove.

4. The system according to claim 3, wherein the latch cams, which are arranged in the inner space of the implant and which engage the ring groove, are configured as circular rings.

5. The system according to claim 1, wherein the tubular implant has, on a side that is opposite of an arc-shaped connection member which is oriented in axial direction, a slit-shaped crack that is oriented in axial direction and wherein separated sides of the ring members are spread in radial direction in relation to each other.

6. The system according to claim 1, wherein the tubular implant is slid with at least one of the ring members onto the distal portion in a jammed manner and wherein the at least one of the ring members, which is provided with a slit-shaped crack, is spread in radial direction for detachment and removal of the distal portion.

7. The system according to claim 1, wherein the tubular implant is slid with at least one of the ring members onto the head piece of the distal portion in a jammed manner and wherein the at least one of the ring members, which is provided with a slit-shaped crack, is spread in radial direction for detachment and removal of the distal portion.

8. The system according to claim 6, wherein the at least one of the ring members, which is provided with the slit-shaped crack, is spread in radial direction by a pressurized injected medium for detachment and removal of the distal portion.

9. The system according to claim 1, wherein a surgical thread is arranged in the tubular implant that penetrates an inner space of the tubular implant in axial direction, and wherein, after removal of the distal portion and the catheter, the surgical thread is loaded against an inner wall of the tubular implant so as to expand a trabecular tissue.

10. The system according to claim 1, wherein the distal portion of the catheter has a length that is 1.5 to 2 times the circumference of a circular Schlemm's canal and wherein the bores of the distal portion are distributed in axial and circumferential direction.

11. The system according to claim 10, wherein the bores, which are arranged at the distal portion and the head piece, have a diameter of 10 µm to 25 µm and operate as nozzles, and wherein the bores are bored with a laser.

12. The system according to claim 11, wherein the laser is an excimer laser.

13. The system according to claim 1, wherein the head piece is configured as a semicircular cap and wherein the head piece has at least one bore that is connected to an inner space of the distal portion and the catheter.

14. The system according to claim 1, wherein the head piece is tapered, starting from an outer diameter of the distal portion in the direction of a distal tip, and wherein the head piece has at least one bore that is connected to an inner space of the distal portion and the catheter.

15. The system according to claim 1, wherein the distal portion is coated at a distal end with a light-reflecting and biocompatible foil and the distal portion has a front portion made of light-reflecting and biocompatible material.

16. The system according to claim 1, wherein the head piece disposed at the distal portion is one of made of light-reflecting and biocompatible material and coated with a light-reflecting and biocompatible foil.

17. The system according to claim 1, wherein the cross-section of the implant is circular and wherein the implant has a connection member, which is oriented in axial direction and approximately circular, and the gaps, which are arranged between individual ones of the ring members, each of which having an opening angle between 280° and 290°.

18. The system according to claim 1, wherein the cross-section of the implant is circular and wherein the implant has two circular connection members, which are diametrically opposite of each other and oriented in axial direction, and wherein the implant has the gaps, which are arranged between individual ones of the ring members, each of which having an opening angle of 90° to 105°.

19. The system according to claim 1, wherein the cross-section of the implant is in the shape of an oval ring and wherein the implant has a connection member, which is oriented in axial direction and arc-shaped, and the gaps arranged between individual ones of the ring members, each of which having an opening angle of 280° to 290°.

20. The system according to claim 19, wherein the cross-section of the implant is in the shape of a double-symmetric oval.

21. The system according to claim 17, wherein the implant, which has the ring members and the gaps, has on the opposite side of the connection member a slit-shaped crack, which is oriented in axial direction.

22. The system according to claim 1, wherein the tubular implant is made of biocompatible flexible material.

23. The system according to claim 22, wherein the biocompatible flexible material is polymeric material having one of a thermal and mechanical shape memory effect.

24. The system according to claim 1, wherein the implant is made of biocompatible material, including one of plastic, non-corroding steel and stainless steel selected from the group consisting of silver, gold, platinum, and nitinol.

25. The system according to claim 1, wherein the implant has a biologically active coating.

26. The system according to claim 25, wherein the biologically active coating is a heparin coating.

* * * * *